(12) United States Patent
Doan et al.

(10) Patent No.: US 8,554,338 B2
(45) Date of Patent: Oct. 8, 2013

(54) MRI-COMPATIBLE IMPLANTABLE LEAD HAVING A HEAT SPREADER AND METHOD OF USING SAME

(75) Inventors: Phong D. Doan, Stevenson Ranch, CA (US); Xiaoyi Min, Thousand Oaks, CA (US); Ingmar Viohl, Canyon Country, CA (US); Xiangqun Chen, Valencia, CA (US); Jose Lepe, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 1007 days.

(21) Appl. No.: 12/613,435

(22) Filed: Nov. 5, 2009

(65) Prior Publication Data

US 2011/0106231 A1 May 5, 2011

(51) Int. Cl.
*A61N 1/04* (2006.01)

(52) U.S. Cl.
USPC .......................................... 607/116

(58) Field of Classification Search
CPC .................................. A61N 1/3718
USPC ......................... 607/116; 606/33
See application file for complete search history.

(56) References Cited

U.S. PATENT DOCUMENTS

| | | |
|---|---|---|
| 3,980,975 A | 9/1976 | Maxon, Jr. et al. |
| 4,236,127 A | 11/1980 | Scherba |
| 5,217,010 A | 6/1993 | Tsitlik et al. |
| 5,428,337 A | 6/1995 | Vinclarelli et al. |
| 7,123,013 B2 | 10/2006 | Gray |
| 7,148,783 B2 | 12/2006 | Parsche et al. |
| 7,174,219 B2 | 2/2007 | Wahlstrand et al. |
| 7,388,378 B2 | 6/2008 | Gray et al. |
| 7,561,906 B2 | 7/2009 | Atalar et al. |
| 7,839,146 B2 | 11/2010 | Gray |
| 7,844,343 B2 | 11/2010 | Wahlstrand et al. |
| 2005/0070972 A1 | 3/2005 | Wahlstrand et al. |
| 2005/0222642 A1 | 10/2005 | Przybyszewski et al. |
| 2005/0222647 A1 | 10/2005 | Wahlstrand et al. |
| 2005/0222658 A1 | 10/2005 | Hoegh et al. |
| 2006/0041294 A1 | 2/2006 | Gray |
| 2006/0247747 A1 | 11/2006 | Olsen et al. |
| 2006/0247748 A1 | 11/2006 | Wahlstrand et al. |
| 2007/0112398 A1 | 5/2007 | Stevenson et al. |
| 2007/0168006 A1 | 7/2007 | Gray |
| 2007/0255377 A1* | 11/2007 | Marshall et al. ............ 607/119 |

(Continued)

FOREIGN PATENT DOCUMENTS

| | | |
|---|---|---|
| EP | 2025361 A1 | 11/2007 |
| EP | 1883449 B1 | 1/2009 |
| WO | 2005102445 A1 | 11/2005 |
| WO | 2005102446 A1 | 11/2005 |

*Primary Examiner* — Christopher D Koharski
*Assistant Examiner* — Michael Carey

(57) ABSTRACT

An implantable lead is provided that comprises a lead body and a header assembly. The lead body has a distal end and a proximal end. The lead body is configured to be implanted in a patient. The header assembly is provided at the distal end of the lead body and includes an internal chamber and a tissue engaging end. An electrode is provided on the header assembly. The electrode is configured to deliver a stimulating pulse. A resonant inductor is located within the chamber in the header assembly. An electrically floating heat spreader is provided on the header assembly. The heat spreader is located proximate to the resonant inductor and is positioned on the header assembly to cover at least a portion of the resonant inductor. The heat spreader is thermally coupled to the resonant inductor to convey thermal energy away from the header assembly.

16 Claims, 10 Drawing Sheets

(56) References Cited

U.S. PATENT DOCUMENTS

| | | |
|---|---|---|
| 2008/0033497 A1 | 2/2008 | Bulkes et al. |
| 2008/0049376 A1 | 2/2008 | Stevenson et al. |
| 2008/0051854 A1 | 2/2008 | Bulkes et al. |
| 2008/0132986 A1 | 6/2008 | Gray et al. |
| 2008/0161886 A1 | 7/2008 | Stevenson et al. |
| 2008/0243218 A1 | 10/2008 | Bottomley et al. |
| 2009/0099440 A1 | 4/2009 | Viohl |
| 2009/0099555 A1 | 4/2009 | Viohl et al. |
| 2009/0281592 A1 | 11/2009 | Vase |
| 2010/0010602 A1 | 1/2010 | Wedan et al. |
| 2010/0016936 A1 | 1/2010 | Stevenson et al. |
| 2010/0023000 A1* | 1/2010 | Stevenson et al. ............... 606/33 |
| 2010/0076538 A1 | 3/2010 | Desai et al. |
| 2010/0114277 A1 | 5/2010 | Zhao et al. |
| 2010/0174348 A1 | 7/2010 | Bulkes et al. |
| 2010/0174349 A1 | 7/2010 | Stevenson et al. |

* cited by examiner

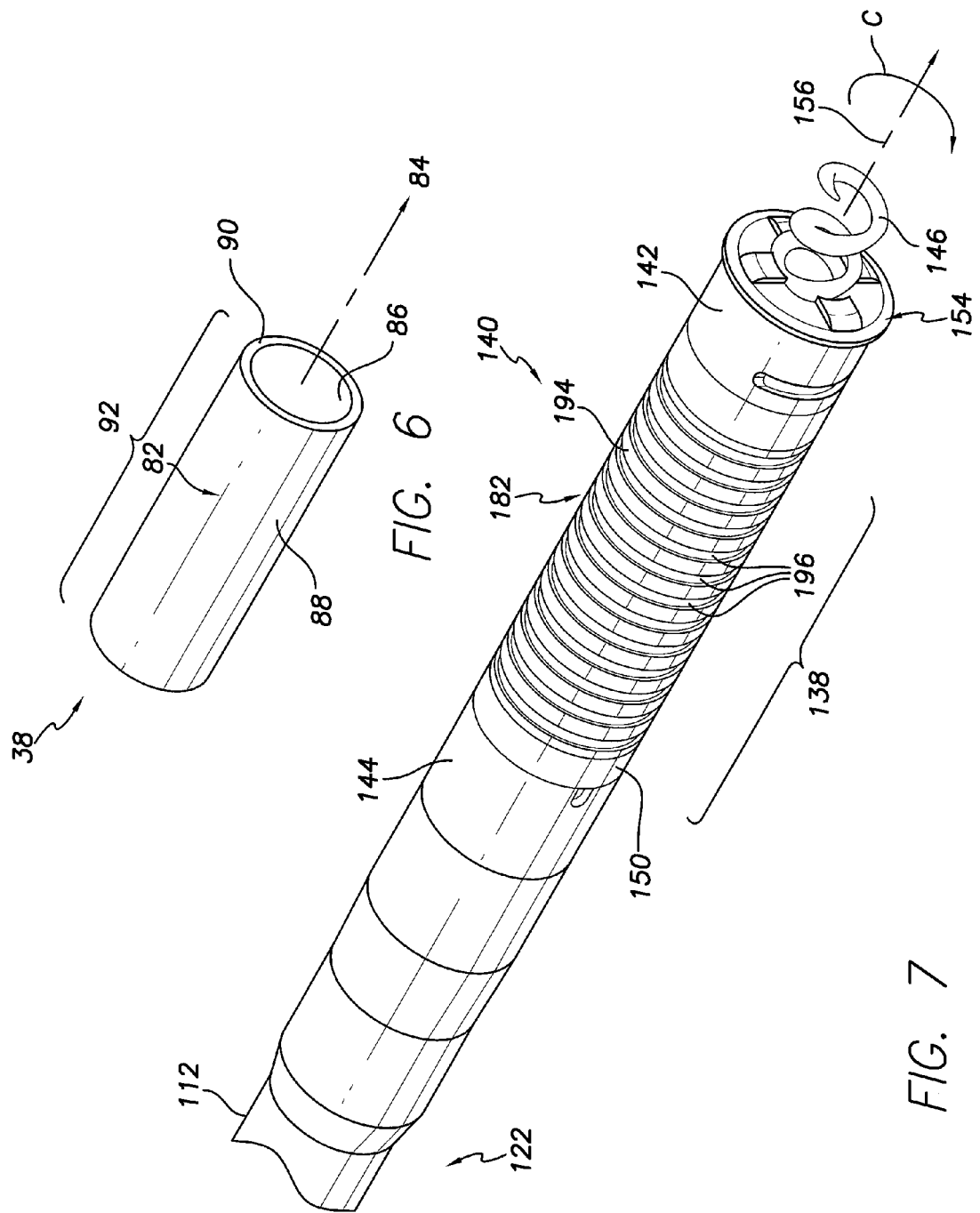

MRI-COMPATIBLE IMPLANTABLE LEAD HAVING A HEAT SPREADER AND METHOD OF USING SAME

CROSS REFERENCE TO RELATED APPLICATIONS

This application is related to U.S. patent application Ser. No. 12/635,340, filed 12/10/2009, titled "MRI-COMPATIBLE IMPLANTABLE LEAD WITH IMPROVED LC RESONANT COMPONENTS".

FIELD OF THE INVENTION

The various embodiments described herein generally relate to implantable leads, and more particularly to MRI-safe implantable leads.

BACKGROUND OF THE INVENTION

An implantable medical device is implanted in a patient to, among other things, monitor electrical activity of a heart and to deliver appropriate electrical and/or drug therapy, as required. Implantable medical devices ("IMDs") include for example, pacemakers, cardioverters, defibrillators, implantable cardioverter defibrillators, an appetite or pain suppression device, and the like. The electrical therapy produced by an IMD may include, for example, pacing pulses, cardioverting pulses, and/or defibrillator pulses to reverse arrhythmias (e.g. tachycardias and bradycardias) or to stimulate the contraction of cardiac tissue (e.g. cardiac pacing) to return the heart to its normal sinus rhythm.

A body implantable lead forms an electrical connection between a patient's anatomy and the IMD. The lead includes a lead body comprising a tubular, flexible biocompatible, biostable insulative sheath or housing, such as formed of silicone rubber, polyurethane or other suitable polymer. One example of a lead body is a bipolar lead having a tip electrode and a ring sensing electrode. Generally bipolar leads include two coaxial conductors with insulation therebetween that are carried within the insulative housing. Another example of a lead body is a cardioverter/defibrillator lead that includes a sensing ring, a shocking right ventricle (RV) electrode, a shocking superior vena cava (SVC) electrode and a tip sensing/pacing electrode. The lead includes a multi-lumen housing, each lumen of which carries a separate conductor through the lead housing to each of the sensing ring, RV electrode, SVC electrode and tip electrode.

Magnetic resonance imaging (MRI) is commonly used as an efficient technique in the diagnosis of many injuries and disorders. MRI scanners provide a non-invasive method for the examination of internal structure and function. During operation, the MRI scanner creates a static magnetic field, a gradient magnetic field and a radio frequency (RF) magnetic field. The static magnetic field may have a field strength of between 0.2 and 3.0 Tesla. A nominal value of 1.5 Tesla is approximately equal to 15,000 Gauss. The time varying or gradient magnetic field may have a maximum strength of approximately 40 milli-Tesla/meters. The RF magnetic field may have a frequency between 8 and 215 MHz. For example, up to 20,000 watts may be produced at 64 MHz in a static magnetic field of 1.5 Tesla.

A concern has arisen regarding the potential interaction between the MRI environment and implantable leads and devices. In particular, implantable leads may experience RF-induced current. The RF induced current has been found to raise the temperature in the leads to undesirable levels.

Heretofore, leads have been proposed for use with MRI-safe implantable medical devices. These proposed leads are coupled to, or have housed therein, a discrete resonant tuning module. The resonant tuning module includes a control circuit for determining a resonance frequency of the implantable device and an adjustable impedance circuit to change the combined resonant frequency of the medical device and the lead. The resonant circuit includes an inductor (L) coupled in parallel with a capacitor (C) to form a discrete LC circuit. The inductance and capacitance values of the inductor and capacitor are tuned approximately to the frequency of an expected RF magnetic field in an MRI scanner.

Using self resonant inductors in the distal portion of a lead has improved electrical performance. However, the resonant current induced at RF frequencies and the resistance within the electrode continues to cause self resonant inductors to heat, particularly in leads that utilize PEEK (i.e. Polyetheretherketones) headers.

Thus, it remains challenging to implement discrete LC and L circuits within leads while still meeting performance requirements. For example, circuit size is a challenge as there is a continued desire to provide circuits that are small enough to be packaged inside the distal portion of a lead yet small LC or L circuits may experience very localized heating.

A need remains for a self resonant inductor solution that avoids undue heating at the header assembly of the lead. It would be further desirable to provide an improved implantable medical lead that may be operated in an MRI environment without the generation of significant heat in the lead. Furthermore, other desirable features and characteristics will become apparent from the subsequent detailed description of the invention and the appended claims, taken in conjunction with the accompanying drawings and this background of the invention.

SUMMARY

In accordance with an embodiment, an implantable lead is provided that comprises a lead body and a header assembly. The lead body has a distal end and a proximal end. The lead body is configured to be implanted in a patient. The header assembly is provided at the distal end of the lead body and includes an internal chamber and a tissue engaging end. An electrode is provided on the header assembly. The electrode is configured to deliver a stimulating pulse. A resonant inductor is located within the chamber in the header assembly. An electrically floating heat spreader is provided on the header assembly. The heat spreader is located proximate to the resonant inductor and is positioned on the header assembly to cover at least a portion of the resonant inductor. The heat spreader is thermally coupled to the resonant inductor to convey thermal energy away from the header assembly.

Optionally, the heat spreader may include a sleeve that wraps about the header assembly. The sleeve extends concentrically about the resonant inductor and is separated from the resonant inductor by the housing wall of the header assembly. Optionally, the heat spreader may include a plurality of annular grooves extending in a circumferential direction about a perimeter of the header assembly. The annular grooves may be spaced apart from one another along the longitudinal axis of the heat spreader. Alternatively, a plurality of longitudinal grooves may be provided on the exterior surface of the heat spreader and oriented to extend in a direction parallel to the longitudinal axis of the header assembly. The longitudinal grooves may be spaced apart from one another about the perimeter of the heat spreader.

BRIEF DESCRIPTION OF THE DRAWINGS

FIG. 6 illustrates an isometric view of an exemplary heat spreader formed in accordance with an embodiment of the present invention.

FIG. 7 illustrates a header assembly formed in accordance with an alternative embodiment.

DETAILED DESCRIPTION

Figure 1:
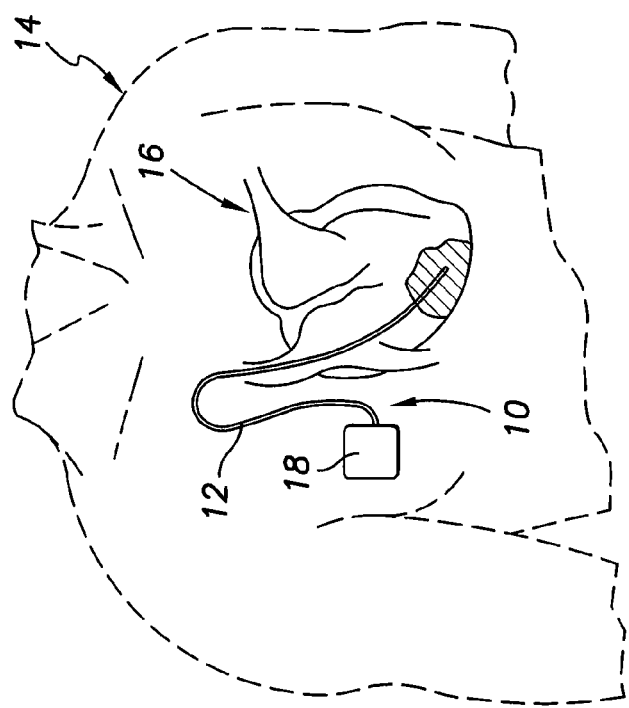
FIG. 1 illustrates an implanted medical system including a pacing lead formed in accordance with an exemplary embodiment.

FIG. 1 illustrates an implantable medical system 10 including an implantable lead 12 formed in accordance with an exemplary embodiment. FIG. 1 depicts a chest cavity 14 in phantom, and a heart 16 within the chest cavity 14. The medical system 10 includes an implantable medical device (IMD) 18 and the lead 12, which are both implanted in the chest cavity 14. Optionally, the medical device 18 may be implanted elsewhere, such as in the patient's abdomen, neck, pelvis regions, etc. In the illustrated embodiment, the lead 12 is a pacing and sensing lead. However, other types of leads may be used in alternative embodiments, such as neuromodulation leads, defibrillation leads, ICD leads, CRT leads, patient monitoring leads and the like. Although the following embodiments are described principally in the context of pacemaker/defibrillator unit capable of sensing and/or pacing pulse delivery, the medical system 10 may be applied to other IMD structures. As further examples, embodiments may be implemented in leads for devices that suppress an individual's appetite, stimulate the patients nervous or muscular systems, stimulate the patient's brain functions, reduce or offset pain associated with chronic conditions and control motor skills for handicap individuals, and the like.

Figure 2:
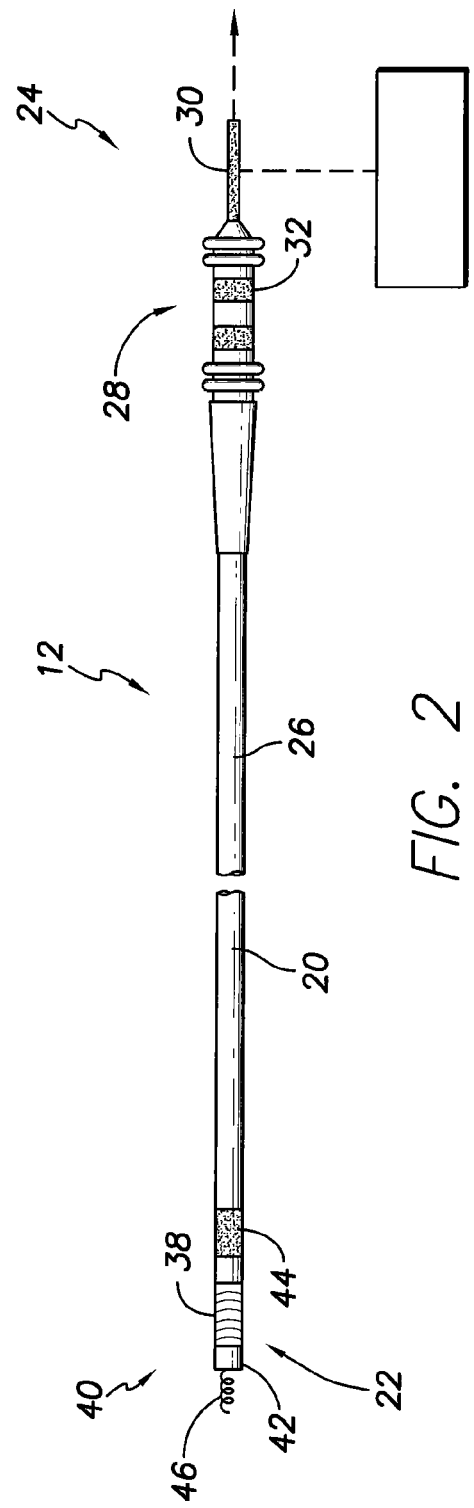
FIG. 2 illustrates the pacing lead shown in FIG. 1.

FIG. 2 illustrates the lead 12 as having an elongated lead body 20 which includes a distal end portion 22 and a proximal end portion 24. The lead body 20 has a length that extends along a longitudinal axis between the distal and proximal end portions 22 and 24. The term longitudinal axis encompasses both linear and non-linear axes. The longitudinal axis of the lead body 20 extends along a curved path that changes as the lead body 20 is flexed, bent and otherwise manipulated. The lead body 20 includes an insulating sheath 26 of a suitable insulative, biocompatible, biostable material such as, for example, PEEK (i.e. Polyetheretherketones), silicone rubber or polyurethane, extending substantially the entire length of the lead body 20.

A connector assembly 28 is provided at the proximal end portion 24 of the lead 12. The connector assembly 28 is configured to be inserted into a receiving orifice in the IMD 18. The connector assembly 28 includes first and second electrical terminals 30, 32 each being connected to respective electrical conductors, such as pacing and sensing electrical conductors, within the lead 12.

A header assembly 40 is provided at the distal end portion 22 of the lead 12. The header assembly 40 includes a tip electrode 42 at the distal end portion 22 and a ring electrode 44 proximate to the distal end portion 22. The tip electrode 42 is electrically connected to the first electrical terminal 30. The ring electrode 44 is connected to the second electrical terminal 32. In an alternative embodiment, the header assembly 40 may include only the tip electrode 42 without a corresponding ring electrode. The header assembly 40 also includes a heat spreader 38, in accordance with embodiments of the present invention, to convey thermal energy away from the header assembly 40.

The header assembly 40 includes a fixation mechanism 46 that functions to interlock the lead 12 within the cardiac tissue at the implantation site and thereby prevent inadvertent displacement of the distal end portion 22 once the lead 12 is implanted. In the illustrated embodiment, the fixation mechanism 46 is represented by a screw-in helix that penetrates the cardiac tissue to anchor the lead 12 thereto.

Figure 3:
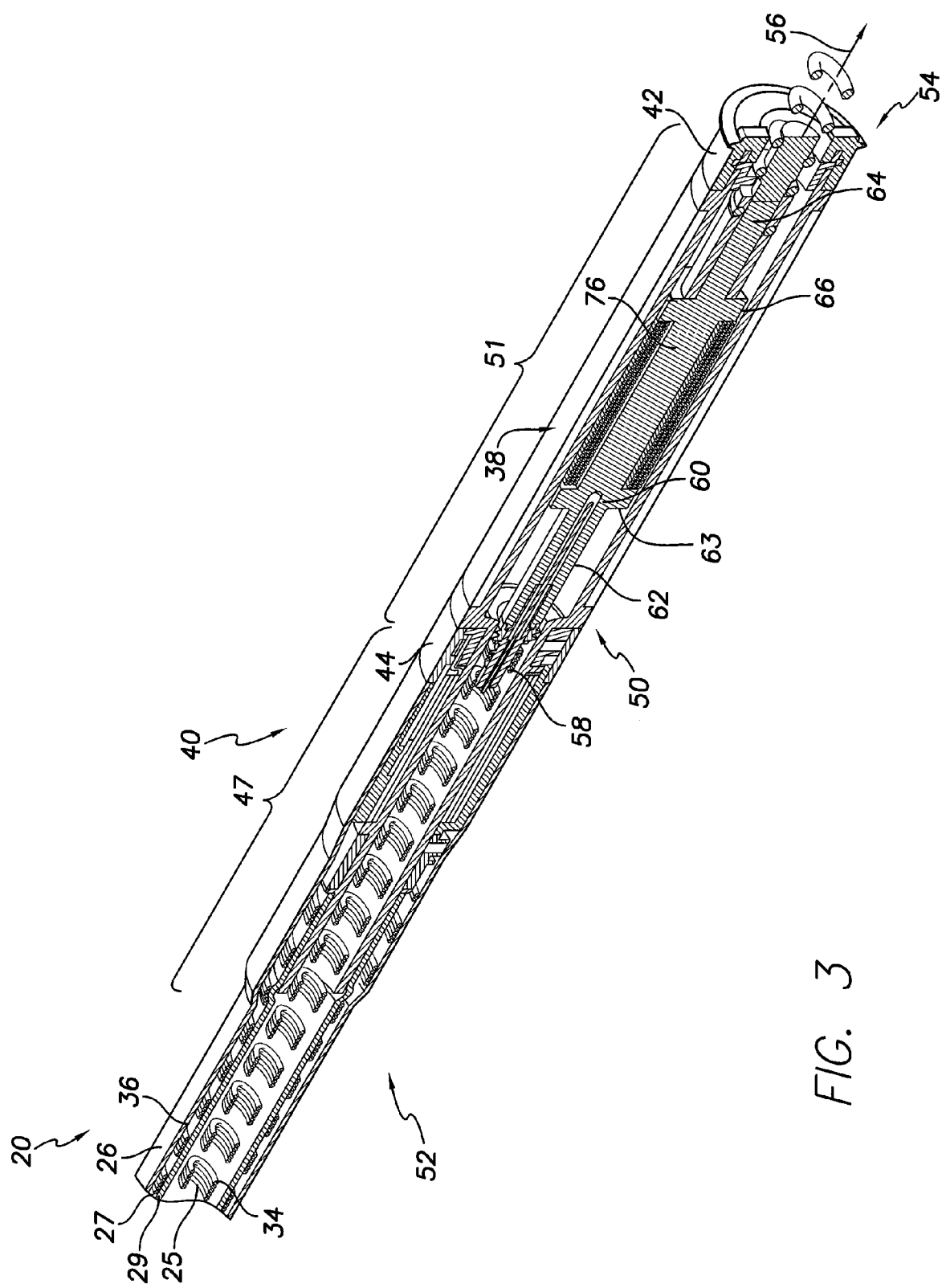
FIG. 3 illustrates a partial cross-sectional view of the distal end portion of the lead body and the header assembly of FIG. 2.

FIG. 3 illustrates a partial cross-sectional view of the distal end portion 22 of the lead body 20 and the header assembly 40 connected thereto. The lead body 20 includes an outer sheath 26 surrounding a central inner lumen 25 and an outer lumen 27. The inner and outer lumens 25 and 27 are separated by an interior wall 29. The inner and outer lumens 25 and 27, and interior wall 29 are formed concentric with one another and extend along the length of the lead body 20. The inner lumen 25 receives a coiled inner conductor 34, while the outer lumen 27 receives a coiled outer conductor 36. The inner and outer conductors 34 and 36 may each be formed of one or more filars/wires. The filars may be bare, coated with insulation or have bare segments and coated segments. For example, in one embodiment, each of the inner and outer conductors 34 and 36 may be formed from a group 5 or 7 coated filars. The structure of the header assembly 40 is discussed below in more detail in connection with FIG. 4.

Figure 4:
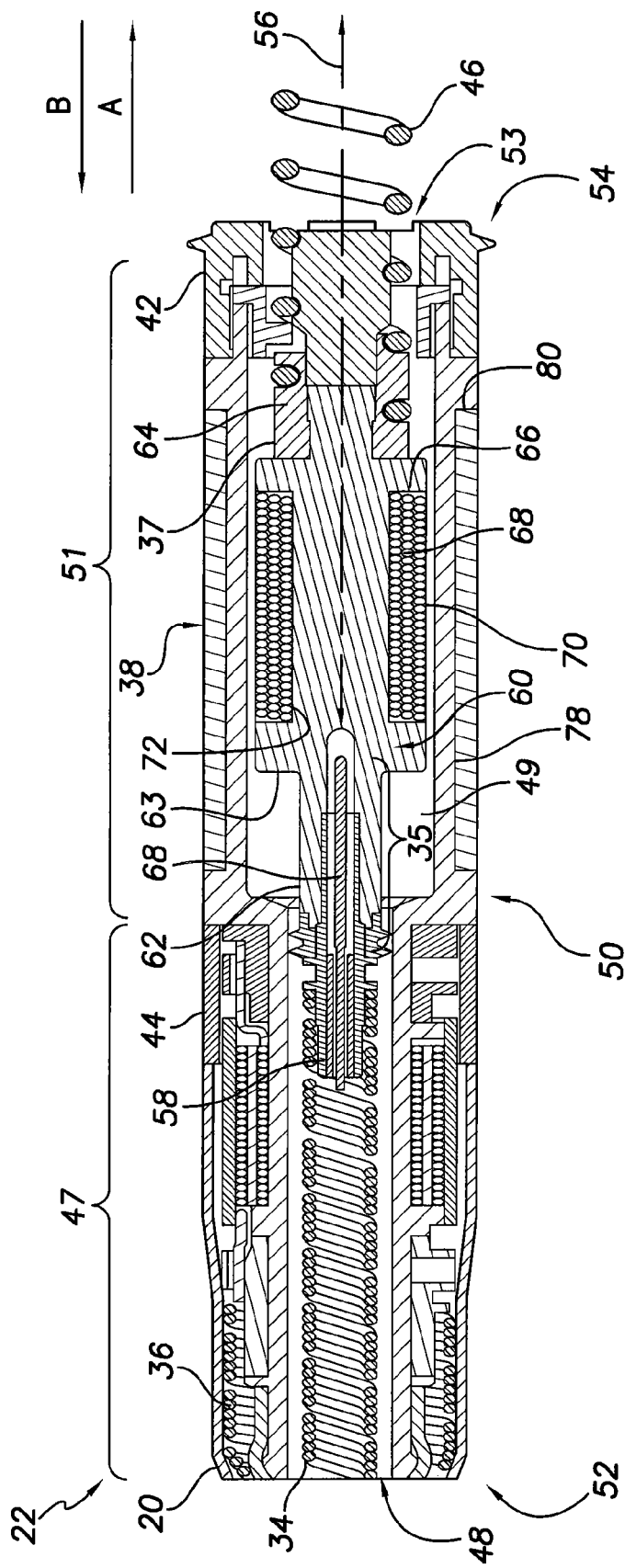
FIG. 4 illustrates a partial cross-section of the header assembly of FIG. 3.

FIG. 4 illustrates a partial cross-section of the header assembly 40. The header assembly 40 includes a housing 50 that is elongated along a longitudinal axis 56. The housing 50 is a hollow, tubular element extending between a lead mating end 52 and a tissue engaging end 54. The lead mating end 52 of the housing 50 is mechanically secured to the distal end portion 22 of the lead body 20, such as by a friction fit, however, other attachment means may be used, such as adhesive, soldering, and the like. In the illustrated embodiment, the outer sheath 26 of the lead body 20 is captured between the housing 50 and a tubular insert to secure the housing 50 to the distal end portion 22 of the lead 12.

The housing 50 is formed of an insulator and is electrically inactive such that the housing 50 does not interact electrically with the cardiac tissue of the patient. Optionally, the housing 50 may be fabricated from a suitable insulative, biocompatible, biostable material. Alternatively, the housing 50 may be fabricated from a biocompatible, biostable metal or metal alloy having an insulative coating surrounding all portions of the housing 50 that may engage the cardiac tissue of the patient. Optionally, the housing 50 may include at least one fluoro-marker (not shown), or other suitable means, for identifying a position of the distal end portion 22 during and/or after implantation within the patient.

The housing 50 includes a rear section 47 and a main body 51 formed integral with one another along the axis 56. The rear section 47 includes an internal lumen 48 that is open at the lead mating end 52. The main body 51 includes a chamber 49 that is joined at one end to the internal lumen 48 and is open at the tissue engaging end 54. The tip electrode 42 is secured on the main body 51 of the housing 50 at the tissue engaging end 52. The tip electrode 42 has an opening 53 through which the fixation mechanism 46 moves. The fixation mechanism 46 of the header assembly 40 is advanced in the direction of arrow A to an extended position to penetrate, and become fixed to, the heart 16 upon implantation. The fixation mechanism 46 is retracted in the direction of arrow B until enclosed in the header assembly 40 to facilitate implantation to a desired location.

The header assembly 40 may retain various electrodes and sensors used by the implanted medical system 10 (shown in FIG. 1) for monitoring and/or pacing the heart 16 (shown in FIG. 1). For example, the header assembly 40 may include more than one ring electrode or may not include any ring electrodes. The tip electrode 42 may operate as a pacing electrode and the ring electrode 44 operates as a sensing electrode. A pacing electrode is configured to provide pacing signals to the tissue of the heart for electrically stimulating the heart tissue by delivering an electrical charge to the heart tissue. A sensing electrode is used to detect electrical activity of the heart. Optionally, the tip electrode 42 may also operate as a sensing electrode.

The rear section 47 of the housing 50 receives the inner conductor 34 within the inner lumen 48. An inductive guide member 60 is provided within the chamber 49 of the main body 51. The inductive guide member 60 moves in the directions of arrows A and B within the chamber 49 with the fixation mechanism 46. The guide member 60 includes a rearward extension 62, a central body 63 and a forward extension 64 arranged along the longitudinal axis 56. The rearward extension 62 holds a transition pin 58. The inner conductor 34 terminates on the transition pin 58 that is connected to a segment 35 of the filar 68 that extends within the rearward extension 62. The fixation mechanism 46 is secured to and held on the forward extension 64. The central body 63 includes an outer surface which holds a resonant inductor 66.

Figure 5:
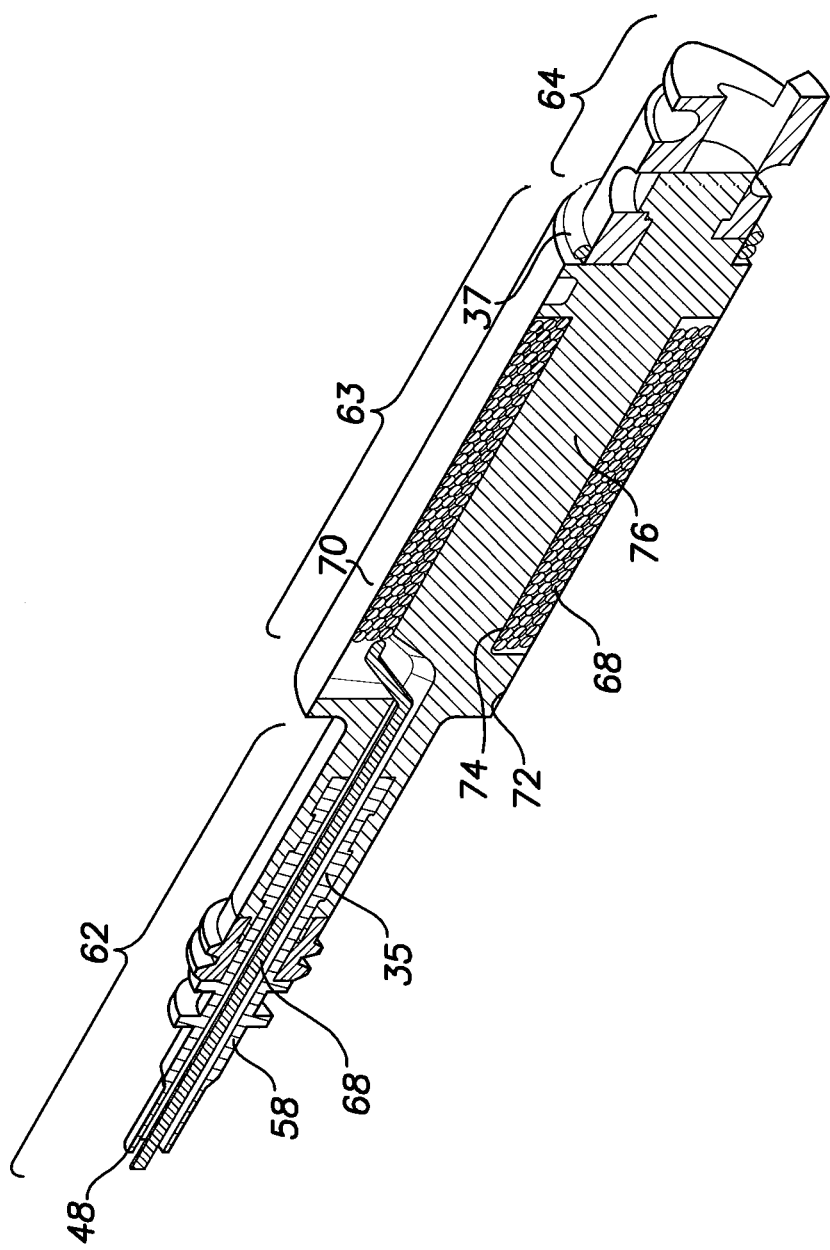
FIG. 5 illustrates a partial isometric view of the guide member and resonant inductor in the header assembly of FIG. 3.

FIG. 5 illustrates a partial isometric view of the guide member 60 and resonant inductor 66. FIG. 5 better illustrates the rearward extension 62, central body 63 and forward extension 64, as well as the transition pin 58 on which the inner conductor 34 terminates on the pin 58. The segment 35 of the filar 68 is secured to the pin 58. The filar 68 extends through the lumen 48 (FIG. 4) in the rearward extension 62 and extends into the central body 63. The central body 63 of the guide member 60 is formed of an insulative material to form a dielectric core 76. The filar 68 wraps about the dielectric core 76 of the central body 63. In the example of FIG. 5, the filar 68 extends continuously about the dielectric core 76 multiple times to form the resonant inductor 66. A peripheral recess 74 extends about the outer wall 72. The filar 68 is wound about the central body 63 and located within the peripheral recess 74 in the outer wall 72. The filar 68 continues onto the forward extension 64 at transition segment 37 and is connected to the tip electrode 42. The filar 68 may comprise one or more filars that are each coated with insulation. Optionally, the filar 68 may include insulation only about the region within the central body 63.

A capacitive component 70 may be provided over the central body 63 and over the resonant inductor 66. The capacitive component 70 and the resonant inductor 66 may be electrically connected in parallel with one another to form a resonant LC circuit. The LC circuit is connected in series at one end with the inner conductor 34 and at the other end with the tip electrode 42 through the segments 35 and 37, respectively. The LC circuit may be tuned by setting the capacitance and inductance of the resonant inductor 64 and the capacitive component 70 to desired levels. The LC circuit may be tuned to a resonance frequency of 64 MHz, 128 MHz and the like, based on the MRI scanner(s) contemplated for use therewith. The component 70 may be a conductive sleeve with good thermal conduction properties. Optionally, the capacitive component 70 may be removed entirely.

Returning to FIG. 4, the housing 50 includes an outer wall 78 that includes a recess 80 thereabout. The heat spreader 38 is located in the recess 80 and wraps about the outer wall 48. The heat spreader 38 is permitted to electrically float in that the heat spreader 38 is not connected to ground (ungrounded) and is not electrically connected to any of the electrodes 42 and 44, nor conductors 34 or 36. The heat spreader 38 is electrically separated from the electrodes 42 and 44, the conductors 34 and 36 and is electrically separated from the resonant inductor 66. The heat spreader 38 is located proximate to the resonant inductor 66 and is positioned at an intermediate position along the header assembly 40 to cover at least a portion of the resonant inductor 66.

The heat spreader 38 is thermally coupled to the resonant inductor 66 through the outer wall 78 of the housing 50 to convey thermal energy away from the header assembly 40. For example, the heat spreader 38 may include a sleeve that wraps about the outer wall 78. The heat spreader 38 extends concentrically about the resonant inductor 66. The housing wall 72 separates the heat spreader 38 from the resonant inductor 66. The housing wall 78 may be formed of a material that has good thermal conduction properties such that energy generated at the resonant inductor 66 readily and easily passes through the outer wall 78 to the heat spreader 38. The tip electrode 42 is located proximate to the tissue engaging end 54 of the header assembly 40, while the heat spreader 38 and resonant inductor 66 are located at an intermediate position along the header assembly 40. The heat spreader 38 is arranged co-axially about and concentric with the resonant inductor 66.

By way of example, the heat spreader 38 may be formed from various materials with good thermal conductive properties that may also be electrically conductive or electrically non-conductive. Sapphire or ceramic materials may be used to form the heat spreader. Sapphire has good thermal conductivity and is lighter than titanium and is biocompatible. The following table illustrates properties of some materials that may be used to form the heat spreader.

| Material | Thermal conductivity | Heat Specificity | Mass density | Dielectric Constant |
|---|---|---|---|---|
| Sapphire | At 20 C. 42 W/(m · K) | 750 J/(kg · K) | $3.97 \times 10^3$ kg/m$^3$ | 9-11 |
| Alumina | 20~40 W/(m · K) | 850~1050 J/(kg · K) | $3.95 \times 10^3$ kg/m$^3$ | 9-10 |
| Ti | 17 W/(mK) | 540 J/(kgK) | $4.5 \times 10^3$ kg/m$^3$ | |

FIG. 6 illustrates an isometric view of an exemplary heat spreader 38 formed in accordance with an embodiment of the present invention. The heat spreader 38 is constructed as a sleeve having a tubular body 82 that extends along a longitudinal axis 84. The body 82 includes an inner surface 86 and an outer surface 88 separated by a radial thickness 90. The body 82 has a length 92. The inner and outer radius, thickness, length and other dimensions of the heat spreader 38 may be adjusted based upon the size, shape and overall design of the lead. In the present example, the length 92 is slightly longer than the length of the resonance inductor 66. Returning to FIG. 4, thermal energy is conveyed radially outward from the resonant inductor 66 and capacitive component 70 through the outer wall 78 of the housing 50 to the inner surface 86. The thermal energy then propagates through the body 82 to the outer surface 88. The thermal energy is dissipated from the outer surface 88 into the surrounding blood and tissue of the heart.

FIG. 7 illustrates a distal portion of a lead formed in accordance with an alternative embodiment. In FIG. 7, the lead 112 includes a header assembly 140 located on the distal end portion 122 thereof. The header assembly 140 generally resembles the header assembly 40 of the figures discussed above, except that an alternative configuration has been provided for a heat spreader 138. More generally, the header assembly 140 includes a tip electrode 142 and a ring electrode 144 provided on a housing 150 of the header assembly 140. The housing 150 includes a tissue engaging end 154, from which a fixation mechanism 146 extends and contracts. The heat spreader 138 has a tubular shaped body 182 that fits in a recess in the housing 150. The body 182 has a contoured outer surface 194.

Figure 8:
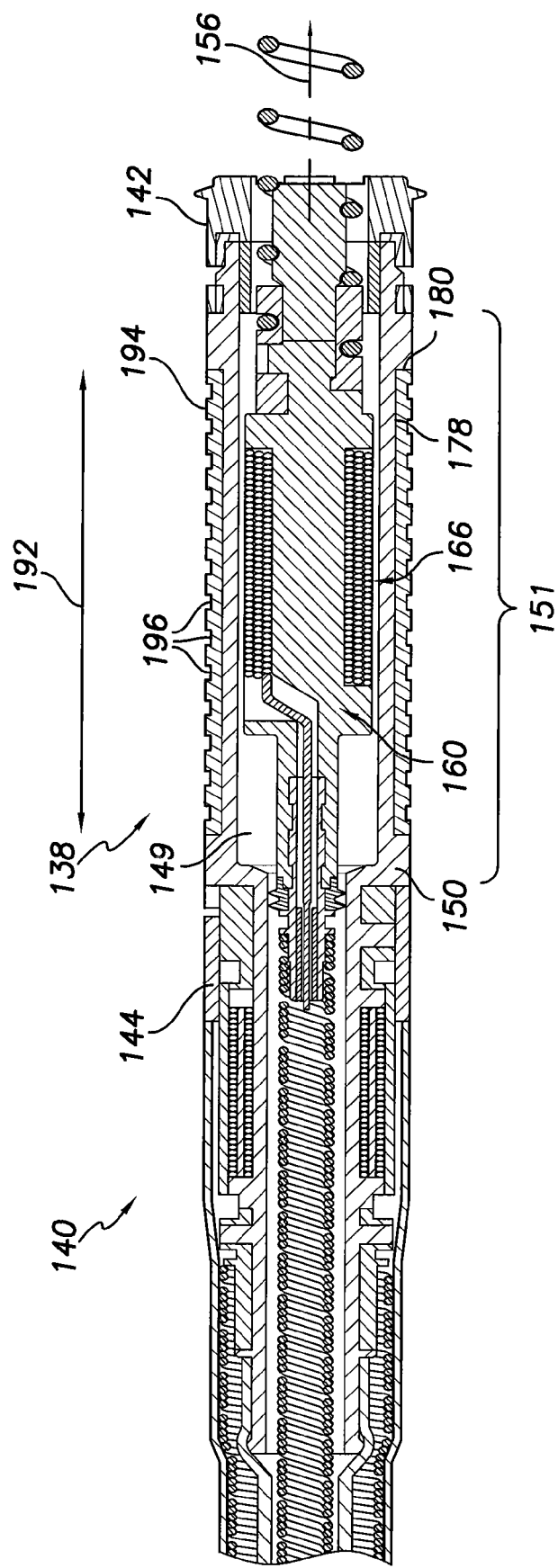
FIG. 8 illustrates a side cross-sectional view of the head assembly of FIG. 7.

FIG. 8 illustrates a side cross-sectional view of the head assembly 140 of FIG. 7 to better illustrate the contoured surface of the heat spreader 138. More specifically, the heat spreader 138 fits within a recess 180 provided in the outer wall 178 of the housing 150. The heat spreader 138 has a length 192 that is dimensioned to enclose and extend beyond opposite ends of the resonant inductor 166. The header assembly 140 includes a ring electrode 144 provided behind the heat spreader 138 and a tip electrode 142 provided proximate the tissue engagement end 154. The housing 150 includes a main body 151 having a chamber 149 provided therein. The chamber 149 receives an inductive guide member 160 that is constructed substantially similar to the inductive guide member 60 illustrated in FIG. 5.

As shown in FIG. 7, the heat spreader 138 includes, in the outer surface 194, a plurality of annular grooves 196 that extend in a circumferential direction (C) about a perimeter of the header assembly 140. The annular grooves 196 are spaced apart from one another along the longitudinal axis 156 of the heat spreader 138 and encourage energy transfer to the surrounding tissue and blood in which the header assembly 140 is positioned.

Figure 9:
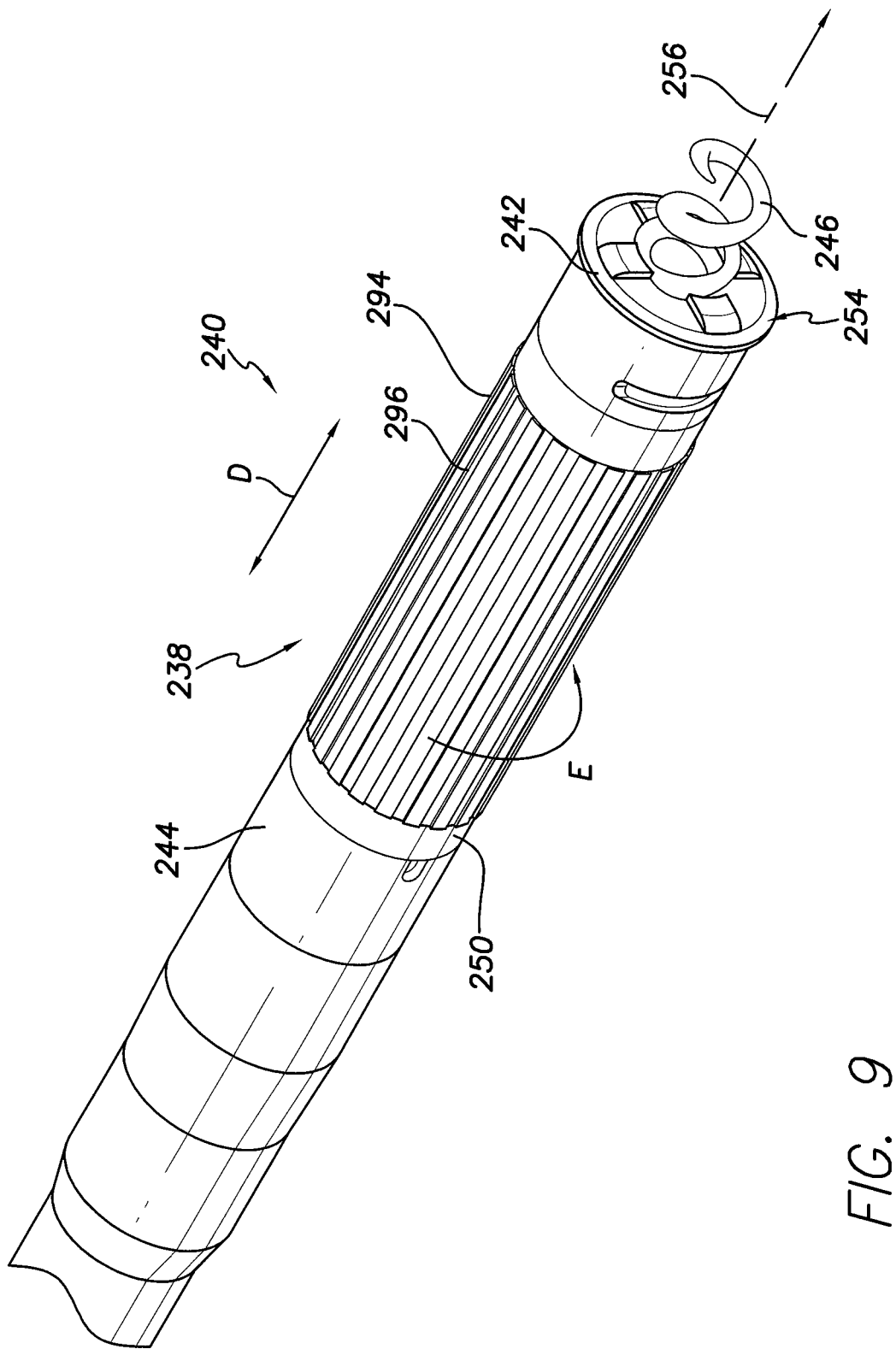
FIG. 9 illustrates a header assembly formed in accordance with an alternative embodiment.

FIG. 9 illustrates an isometric view of a header assembly 240 formed in accordance with an alternative embodiment. The header assembly 240 includes a housing 250 with a tissue engagement end 254, from which a fixation mechanism 246 extends and contracts. A tip electrode 242 and a ring electrode 244 are provided on the housing 250. A heat spreader 238 is also provided on the housing 250 and is positioned between the tip and ring electrodes 242 and 244. The heat spreader 238 has an outer surface 294 with a plurality of longitudinal grooves 296 that extend in direction D parallel to the longitudinal axis 256 of the header assembly. The longitudinal grooves 296 are spaced apart from one another in the direction denoted by arc E about a perimeter of the heat spreader 238. The longitudinal grooves 296 facilitate energy transfer between the heat spreader 238 and the surrounding blood or tissue in which the header assembly 240 is located.

Figure 10:
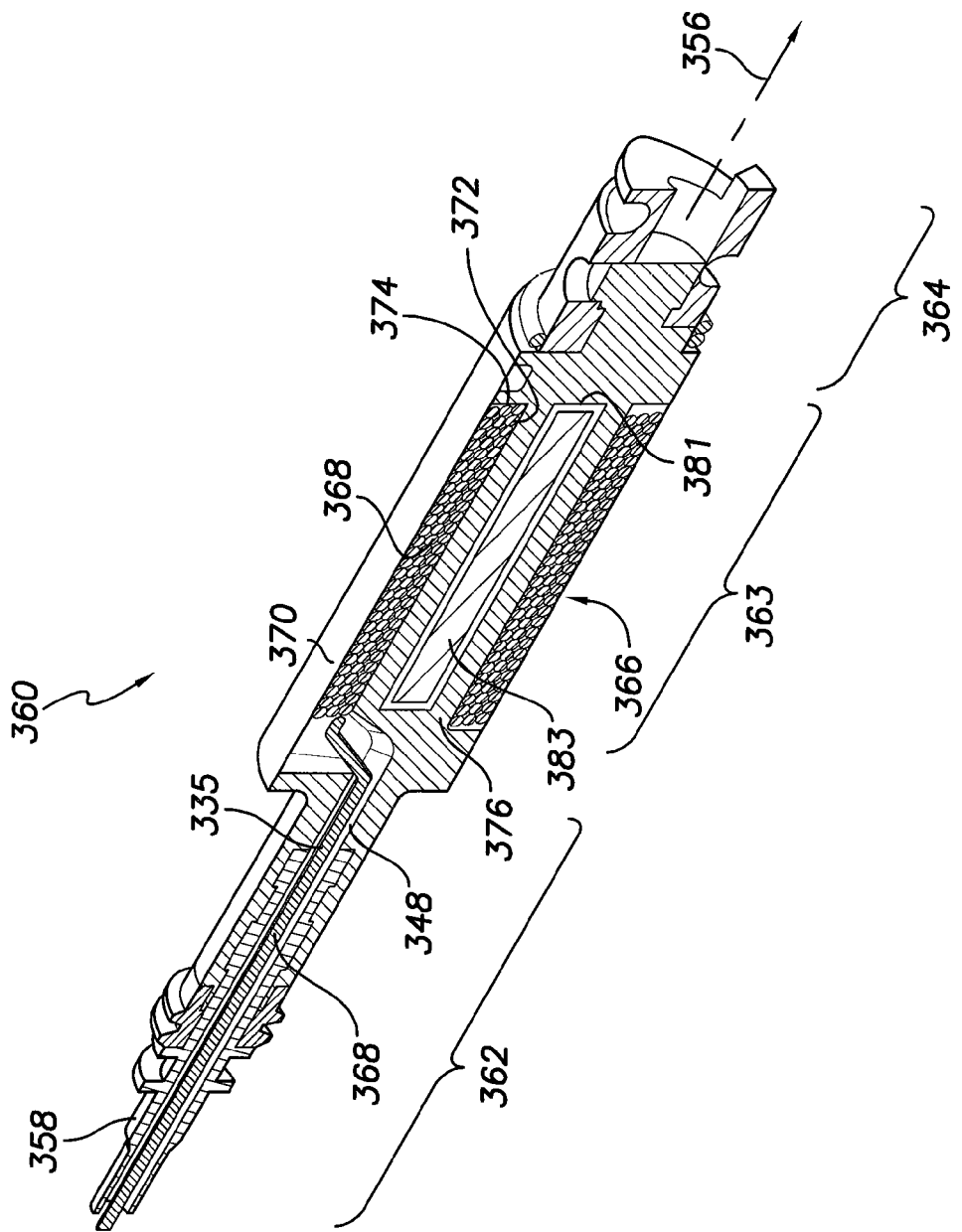
FIG. 10 illustrates a partial isometric view of an inductive guide member formed in accordance with an alternative embodiment.

FIG. 10 illustrates a partial isometric view of an inductive guide member 360 formed in accordance with an alternative embodiment. The inductive guide member 360 may be provided with any of the header assemblies discussed herein or alternative lead configurations. The inductive guide member 360 includes a rearward extension 362, a central body 363 and a forward extension 364. An inner conductor (e.g., 34 in FIG. 3) is terminated onto a pin 358. A segment 335 of a filar 368 is secured to the pin 358. The filar 368 extends through a lumen 348 in the rearward extension 362 and extends into the main central body 363. The central body 363 is formed of an insulated material to form a dielectric core 376. The filar 368 wraps about the dielectric core 376 to form the resonant inductor 366. The central body 363 includes a peripheral recess 374 formed in the outer wall 372 thereof. The filar 368 wraps about the recess 374. A capacitive component 370 is provided over the central body 363 and over the resonant inductor 366.

In the embodiment of FIG. 10, a secondary or inner heat spreader 383 is provided in a cavity 381 within the dielectric core 376. The cavity 381 receives the second heat spreader 383 which is dimensioned to extend along the central body 363 and have a cross-section (when viewed along the longitudinal axis 356) that substantially resembles the cross-section of the dielectric core 376. For example, when the dielectric core 376 has a circular cross-section, the secondary heat spreader 383 similarly has a circular cross-section. In the foregoing example, the secondary heat spreader 383 may have a cylindrical or pin shape. The secondary heat spreader 383 may also function as a core for the resonant inductor 366. The inner and outer heat spreaders extend along the longitudinal axis of the header assembly.

Figure 11:
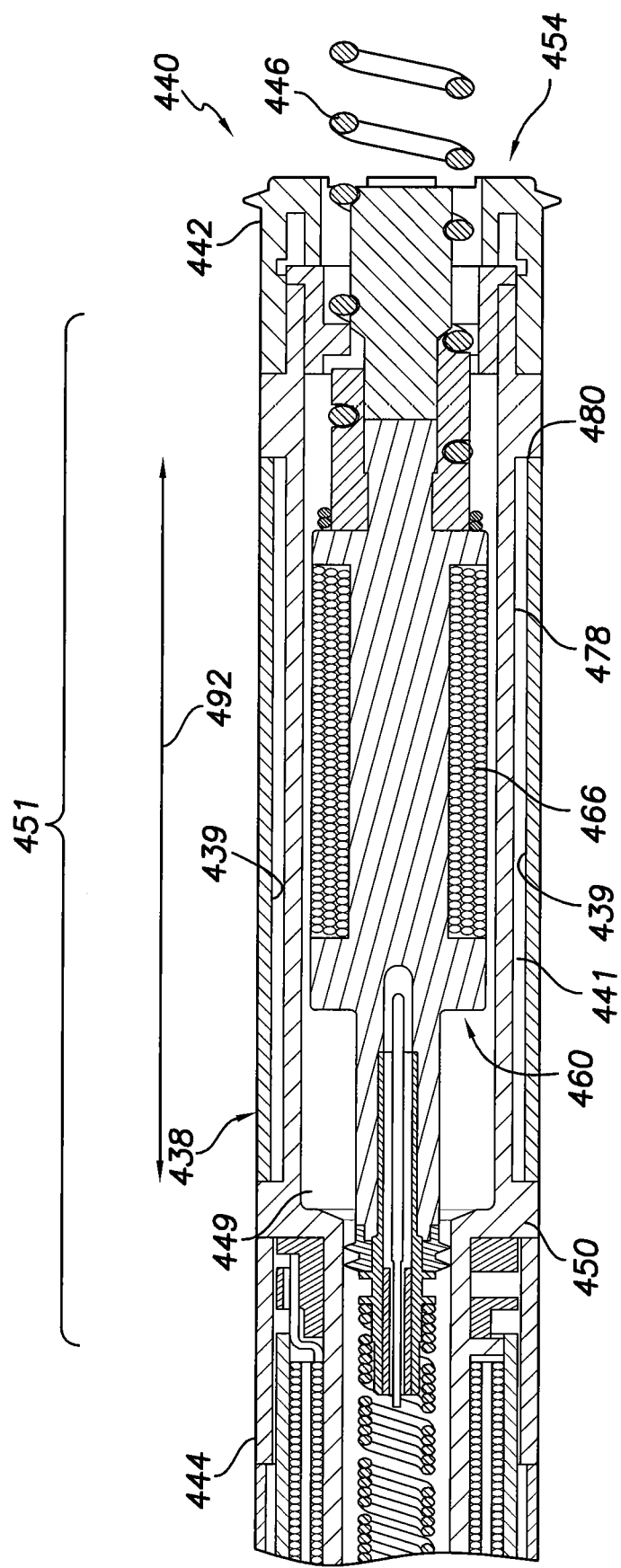
FIG. 11 illustrates a side cross-sectional view of a head assembly formed in accordance with an alternative embodiment.

FIG. 11 illustrates a side cross-sectional view of a head assembly 440 formed in accordance with an alternative embodiment. In FIG. 11, the header assembly 440 generally resembles the header assembly 40 of the figures discussed above, except that an alternative configuration has been provided for a heat spreader 438. More generally, the header assembly 440 includes a tip electrode 442 and a ring electrode 444 provided on a housing 450 of the header assembly 440. The housing 450 includes a tissue engaging end 454, from which a fixation mechanism 446 extends and contracts. The heat spreader 438 has a tubular shaped body. The heat spreader 438 fits within a recess 480 provided in the outer wall 478 of the housing 450. The heat spreader 438 has a length 492 that is dimensioned to enclose and extend beyond opposite ends of a resonant inductor 466. The housing 450 includes a main body 451 having a chamber 449 provided therein. The chamber 449 receives an inductive guide member 460 that is constructed substantially similar to the inductive guide member 60 illustrated in FIG. 5.

In the embodiment of FIG. 11, the heat spreader 438 is held in the housing 450 such that an inner surface 439 on the heat spreader is spaced apart from an outer wall 478 of the recess 480. The gap between the inner surface 439 on the heat spreader 438 and the outer wall 478 in the recess 480 creates an air gap 441. The air gap 441 facilitates even distribution of the heat generated by the inductive guide member 460 across the heat spreader 438.

Figure 12:
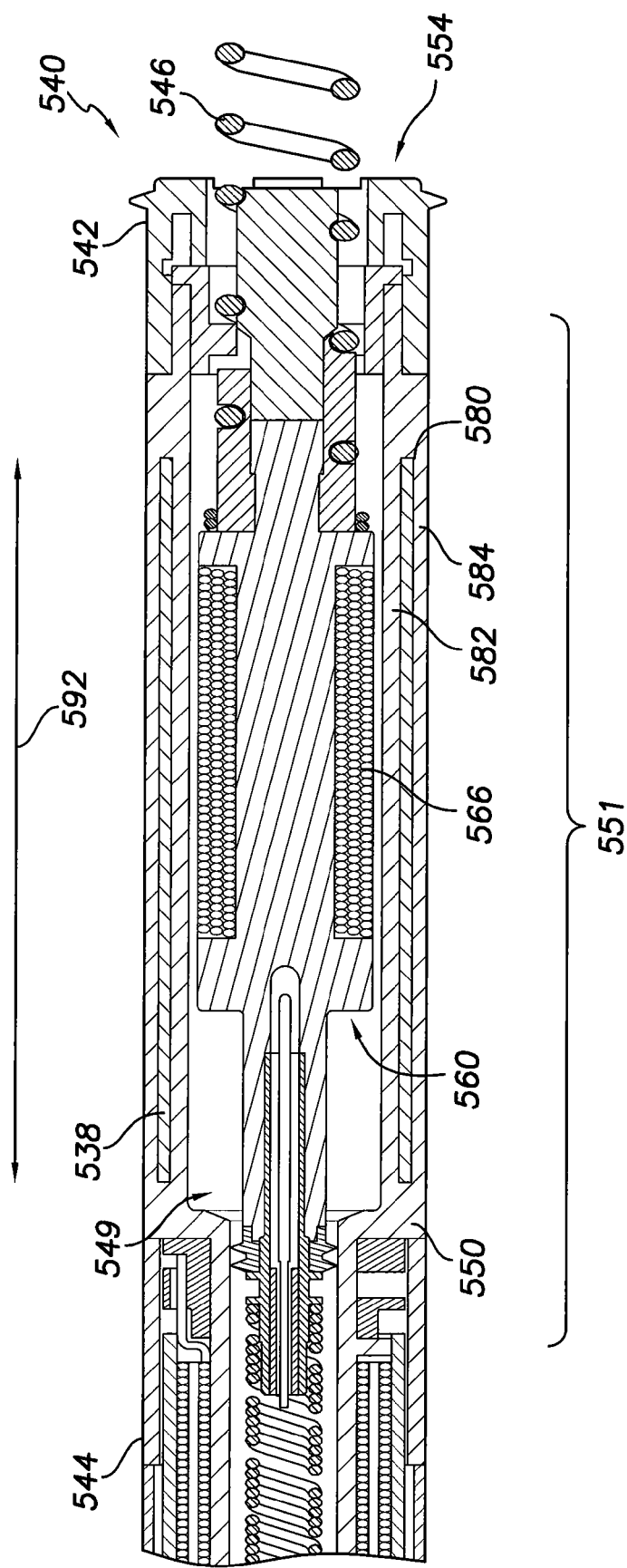
FIG. 12 illustrates a side cross-sectional view of a head assembly formed in accordance with an alternative embodiment.

FIG. 12 illustrates a side cross-sectional view of a head assembly 540 formed in accordance with an alternative embodiment. The header assembly 540 generally resembles the header assembly 40 of the figures discussed above, except that an alternative configuration has been provided for a heat spreader 538. More generally, the header assembly 540 includes a tip electrode 542 and a ring electrode 544 provided on a housing 550 of the header assembly 540. The housing 550 includes a tissue engaging end 554, from which a fixation mechanism 546 extends and contracts. The heat spreader 538 has a tubular shaped body.

The housing 550 includes a main body 551 having a chamber 549 provided therein. The chamber 549 receives an inductive guide member 560 that is constructed substantially similar to the inductive guide member 60 illustrated in FIG. 5. The heat spreader 538 is located and sealed within a cavity 580 created within the main body 551 of the housing 550. The heat spreader 538 has a length 592 that is dimensioned to enclose and extend beyond opposite ends of the resonant inductor 566.

The cavity 580 is surrounded by inner and outer layers 582 and 584 that are formed integral with the housing 550. The inner and outer layers 582 and 584 extend concentrically with one another about the housing 550 in a generally cylindrical or tubular shape. The inner and outer layers 582 and 584 are separated from one another by a distance to define the cavity 580 therebetween. The heat spreader 538 is hermetically sealed and embedded within the cavity 580 between the inner and outer layers 582 and 584 to isolate the heat spreader 538 from surrounding tissue and blood. The heat spreader 538 receives heat from the inductive guide member 560, distributes the heat along the length of the heat spreader 538 and allows the heat to radially disperse outward therefrom through the outer layer 584 of the housing 550.

The above discussed embodiments for heat spreaders may be used in various types of leads, such as active or passive leads. For example, the heat spreader may be implemented in a pacing lead, an ICD lead, a CRT lead, a non-cardiac lead, a neurostimulation lead and the like.

In accordance with various embodiments provided herein, a heat spreader is provided at the distal end of the lead near the components within the header on the lead in order to reduce the temperature at the interface between the lead body and the surrounding fluid. Exemplary embodiments for the heat spreader may include a metal sleeve or a metal core. In alternative configurations, the heat spreader may be constructed of another bio-compatible material that has good heat transfer characteristics. In certain embodiments, the heat spreader is located proximate to a resonant inductor. In certain embodiments, the heat spreader is provided as an electrically floating component in that the heat spreader is not connected to a ground or to any other conductor extending along the lead. Optionally, a separate conductor may be provided within the lead body to connect to the heat spreader to afford grounding or induce a desired bias.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. An implantable lead, comprising:
a lead body, having a distal end and a proximal end, configured to be implanted in a patient;
a header assembly provided at the distal end of the lead body, the header assembly including a tissue engaging end and a housing having an internal chamber and an outer surface that includes a peripheral recess extending thereabout;
an electrode provided on the header assembly, the electrode configured to deliver stimulating pulses;
a resonant inductor located within the chamber of the header housing; and
an electrically floating heat spreader being located in the peripheral recess about the exterior perimeter of the housing, the heat spreader being located proximate to the resonant inductor and positioned on the header assembly to cover at least a portion of the resonant inductor, the heat spreader being thermally coupled to the resonant inductor to convey thermal energy away from the resonant inductor and the header assembly.

2. The implantable lead of claim 1, wherein the heat spreader includes a sleeve that wraps about a housing wall of the header assembly.

3. The implantable lead of claim 1, wherein the heat spreader extends concentrically about the resonant inductor, the header assembly having a housing wall that separates the heat spreader from the resonant inductor.

4. The implantable lead of claim 1, wherein the resonant inductor includes at least one insulated filar that is helically wound about a housing of the header assembly.

5. The lead of claim 1, wherein the header assembly includes a housing with an opening at the tissue engaging end, and a fixation member provided in the chamber proximate the tissue engaging end, the resonant inductor movably located in the chamber.

6. The lead of claim 1, wherein the electrode is located proximate to the tissue engaging end of the header assembly, while the heat spreader and resonant inductor are located at an intermediate position along the header assembly.

7. The lead of claim 1, wherein the electrode constitutes one of a tip, ring and coil electrode, the resonant inductor being electrically connected to the electrode.

8. The lead of claim 1, wherein the housing includes outer wall with a central lumen therethrough, the outer wall being positioned between and electrically separating the heat spreader from the resonant inductor.

9. The lead of claim 1, wherein the resonant inductor includes capacitive components and inductive components connected in series and tuned to a resonant frequency of an MR scanner.

10. The lead of claim 1, wherein the heat spreader is ungrounded and electrically isolated from the electrode and resonant inductor.

11. The lead of claim 1, wherein the head assembly is a PEEK lead header.

12. An implantable lead, comprising:
- a lead body, having a distal end and a proximal end, configured to be implanted in a patient;
- a header assembly provided at the distal end of the lead body, the header assembly including an internal chamber and a tissue engaging end;
- an electrode provided on the header assembly, the electrode configured to deliver stimulating pulses;
- a resonant inductor located within the chamber of the header assembly; and
- an electrically floating heat spreader provided on the header assembly, the heat spreader being located proximate to the resonant inductor and positioned on the header assembly to cover at least a portion of the resonant inductor, the heat spreader being thermally coupled to the resonant inductor to convey thermal energy away from the header assembly, wherein the resonant inductor includes an insulated coil wrapped about a dielectric core, the core having a cavity formed therein and extending along the resonant inductor, the cavity retaining an inner heat spreader.

13. The lead of claim 1, wherein the heat spreader extends along a longitudinal axis of the header assembly, the heat spreader having a plurality of annular grooves wrapping about the longitudinal axis around a perimeter of the heat spreader.

14. The lead of claim 1, wherein the heat spreader extends along a longitudinal axis of the header assembly, the heat spreader having a plurality of longitudinal grooves extending in a direction parallel to the longitudinal axis and spaced apart from one another about a perimeter of the heat spreader.

15. The lead of claim 1, wherein the heat spreader is held in a recess in a housing of the header assembly such that an inner surface of the heat spreader is spaced apart from an outer wall of the housing by an air gap.

16. An implantable lead, comprising:
- a lead body, having a distal end and a proximal end, configured to be implanted in a patient;
- a header assembly provided at the distal end of the lead body, the header assembly including an internal chamber and a tissue engaging end;
- an electrode provided on the header assembly, the electrode configured to deliver stimulating pulses;
- a resonant inductor located within the chamber of the header assembly; and
- an electrically floating heat spreader provided on the header assembly, the heat spreader being located proximate to the resonant inductor and positioned on the header assembly to cover at least a portion of the resonant inductor, the heat spreader being thermally coupled to the resonant inductor to convey thermal energy away from the header assembly, wherein the header assembly has a housing with a cavity formed therein, the heat spreader being embedded within the cavity in the housing.

* * * * *